(12) United States Patent
Zhu et al.

(10) Patent No.: US 10,490,854 B2
(45) Date of Patent: Nov. 26, 2019

(54) ELECTROLYTE ADDITIVES AND ELECTRODE MATERIALS FOR HIGH TEMPERATURE AND HIGH VOLTAGE OPERATION

(71) Applicant: Wildcat Discovery Technologies, Inc., San Diego, CA (US)

(72) Inventors: Ye Zhu, San Diego, CA (US); Gang Cheng, San Diego, CA (US); Deidre Strand, San Diego, CA (US); Bin Li, San Diego, CA (US); Tanghong Yi, San Diego, CA (US)

(73) Assignee: Wildcat Discovery Technologies, Inc., San Diego, CA (US)

( * ) Notice: Subject to any disclaimer, the term of this patent is extended or adjusted under 35 U.S.C. 154(b) by 0 days.

(21) Appl. No.: 15/639,919

(22) Filed: Jun. 30, 2017

(65) Prior Publication Data
US 2018/0006330 A1    Jan. 4, 2018

Related U.S. Application Data

(60) Provisional application No. 62/356,857, filed on Jun. 30, 2016.

(51) Int. Cl.
| | | |
|---|---|---|
| *H01M 10/0567* | (2010.01) | |
| *C08F 212/08* | (2006.01) | |
| *C08F 212/36* | (2006.01) | |
| *H01M 4/52* | (2010.01) | |
| *H01M 4/62* | (2006.01) | |
| *H01M 10/0525* | (2010.01) | |
| *H01M 10/0565* | (2010.01) | |
| *C01B 33/12* | (2006.01) | |
| *C07F 9/09* | (2006.01) | |
| *H01M 4/02* | (2006.01) | |
| *H01M 4/525* | (2010.01) | |

(52) U.S. Cl.
CPC ....... *H01M 10/0567* (2013.01); *C08F 212/08* (2013.01); *C08F 212/36* (2013.01); *H01M 4/523* (2013.01); *H01M 4/62* (2013.01); *H01M 4/622* (2013.01); *H01M 10/0525* (2013.01); *H01M 10/0565* (2013.01); *C01B 33/12* (2013.01); *C07F 9/092* (2013.01); *C07F 9/095* (2013.01); *H01M 4/525* (2013.01); *H01M 2004/026* (2013.01); *H01M 2004/027* (2013.01)

(58) Field of Classification Search
CPC ......... H01M 10/0567; H01M 10/0525; H01M 10/0565; H01M 4/523; H01M 4/62
See application file for complete search history.

(56) References Cited

U.S. PATENT DOCUMENTS

| | | |
|---|---|---|
| 6,461,772 B1 | 10/2002 | Miyake et al. |
| 2005/0095504 A1 | 5/2005 | Kim et al. |
| 2006/0003211 A1 | 1/2006 | Sun et al. |

(Continued)

*Primary Examiner* — Jimmy Vo
(74) *Attorney, Agent, or Firm* — Philip S. Hof; The Small Patent Law Group, LLC

(57) ABSTRACT

A battery including an anode, a cathode, a separator, and a liquid electrolyte including a lithium salt, a non-aqueous solvent, and an additive compound including a functionalized matrix having a polymer or copolymer or silica. The cathode material can be an NMC or LCO material. The electrode formed from the cathode or anode material can include a matrix additive. The matrix additive can be adhered to the separator or other inert component of the battery.

19 Claims, 9 Drawing Sheets

(56) References Cited

U.S. PATENT DOCUMENTS

| | | | |
|---|---|---|---|
| 2009/0035646 A1* | 2/2009 | Mikhaylik | H01M 10/052 |
| | | | 429/50 |
| 2012/0107695 A1 | 5/2012 | Lee et al. | |
| 2012/0244419 A1* | 9/2012 | Kwak | H01M 10/0525 |
| | | | 429/163 |
| 2016/0294005 A1* | 10/2016 | Lee | H01M 4/382 |

* cited by examiner

ELECTROLYTE ADDITIVES AND ELECTRODE MATERIALS FOR HIGH TEMPERATURE AND HIGH VOLTAGE OPERATION

BACKGROUND OF THE INVENTION

The present invention is in the field of battery technology and, more particularly, in the area of additives for use with high-energy electrolytes and electrodes in electrochemical cells.

A liquid electrolyte serves to transport ions between electrodes in a battery. Organic carbonate-based electrolytes are most commonly used in lithium-ion ("Li-ion") batteries and, more recently, efforts have been made to develop new classes of electrolytes based on sulfones, silanes, and nitriles. Unfortunately, these conventional electrolytes typically cannot be operated at high voltages, since they are unstable above 4.2 V or other high voltages. At high voltages, conventional electrolytes can decompose, for example, by catalytic oxidation in the presence of cathode materials, to produce undesirable products that affect both the performance and safety of a battery. Conventional electrolytes may also be degraded by reduction by the electrodes when the cells are charged.

Solvents, salts, or additives have been incorporated into the electrolyte to decompose on the electrode to form a protective film called a solid electrolyte interphase (SEI). Depending on the exact chemical system, this film can be composed of organic or inorganic lithium salts, organic molecules, oligomers, or polymers. Often, several components of the electrolyte are involved in the formation of the SEI (e.g., lithium salt, solvent, and additives). As a result, depending on the rate of decomposition of the different components, the SEI can be more or less homogenous.

For high-energy cathode materials, electrolyte stability remains a challenge. Recently, the need for higher performance and high capacity lithium ion secondary batteries used for power sources is dramatically increasing. Lithium transition metal oxides such as $LiCoO_2$ ("LCO") and $LiNi_{0.33}Mn_{0.33}Co_{0.33}O_2$ ("NMC") are state-of-the-art high-energy cathode materials used in commercial batteries. Yet only about 50% of the theoretical capacity of LCO or NMC cathodes can be used with stable cycle life. To obtain the higher capacity, batteries containing these high-energy materials need to be operated at higher voltages, such as voltages up to about 4.7V. However, above about 4.2V, conventional electrolytes degrade and this leads to a significant deterioration of the cycle life. Further, the decomposition of the electrolyte at higher voltages can generate gas (such as $CO_2$, $O_2$, ethylene, $H_2$) and acidic products, both of which can damage a battery. These effects are further enhanced in "high nickel" NMC compositions such as $LiNi_{0.6}Mn_{0.2}Co_{0.2}O_2$ or $LiNi_{0.8}Mn_{0.1}Co_{0.1}O_2$ or others, which can provide higher capacities, due to the electrochemical nature of the nickel.

Many of these same challenges occur when a battery is operated at high temperature. That is, conventional electrolytes can be decomposed by oxidation or may be degraded by reduction at high temperature analogous to the way these mechanisms affect the electrolytes at high voltage. Other parasitic reactions can also occur at elevated temperature.

Lithium ion batteries operating at higher voltage, such as greater than 4.25V, are needed in order to meet increasing energy density requirements for automobile applications. However, the high voltage conditions can result in shortened cycle life and safety concerns, such as an increased risk of fire. Current state of the art electrolytes are known to be unstable at high voltages, especially at elevated temperatures. Electrolyte formulations currently used in most commercial lithium-ion batteries are alkyl carbonate based electrolytes, using $LiPF_6$ as a salt. Formation of acidic species from thermal decomposition of $LiPF_6$, as well as oxidative electrolyte decomposition at higher voltages, results in transition metal dissolution from the cathode surface. The resulting metal ions migrate to the anode where they are reduced on the anode surface, causing anode SEI decomposition and/or reformation. The SEI decomposition and/or reformation can then lead to increased lithium ion consumption as well as significant growth in the electrical impedance of the cell, both of which are undesirable.

Current electrolyte formulations that use $LiPF_6$ can reach a high specific conductivity, about 10 mS $cm^{-1}$ at room temperature, for example. These electrolyte formulations are typically able to passivate an aluminum current collector at the cathode and thereby prevent aluminum corrosion at high voltages. However, in presence of lithiated graphite and/or delithiated transition metal oxides, $LiPF_6$ has limited thermal stability. This limited thermal stability negatively affects the usefulness of current electrolyte formulations in large-scale lithium ion batteries for electric vehicle (EV) applications. It is well known that $LiPF_6$ will undergo thermal decomposition reactions to generate the strong Lewis acids, such as $PF_5$ or even protic acid HF if even trace amounts of water are present. The resulting acidic species often trigger a number of undesirable chemical reactions, such as ring-opening reactions of cyclic carbonates and acid-base reactions with transition metal oxides in the cathode. These undesirable reactions often result in continuous consumption of electrolyte as well as lithium ions, which ultimately leads to capacity fade and impedance growth during cycling, especially cycling at elevated temperatures.

As disclosed herein, these challenges and others are addressed in high energy lithium-ion batteries operation at high voltage and at high temperature.

BRIEF SUMMARY OF THE INVENTION

Certain embodiments relate to a battery including an anode, a cathode, a separator, and a liquid electrolyte including a lithium salt, a non-aqueous solvent, and an additive compound including a functionalized matrix having a polymer or copolymer or silica. In some embodiments, the cathode material can be an NMC or LCO material. In some embodiments, the electrode formed from the cathode or anode material can include a functionalized matrix additive. In another embodiment, the functionalized matrix additive can be adhered to the separator or other inert component of the battery.

Certain embodiments include methods making, using, and conditioning such batteries for use.

Other aspects and embodiments of the invention are also contemplated. The foregoing summary and the following detailed description are not meant to restrict the invention to any particular embodiment but are merely meant to describe some embodiments of the invention.

DETAILED DESCRIPTION OF THE INVENTION

Figure 1:
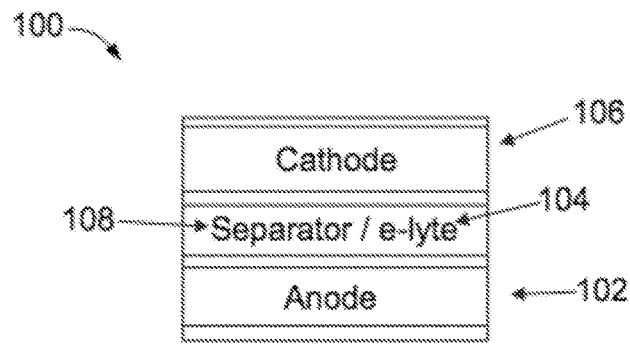
FIG. 1 illustrates a lithium ion battery implemented according to an embodiment of the invention.

The following definitions apply to some of the aspects described with respect to some embodiments of the invention. These definitions may likewise be expanded upon herein. Each term is further explained and exemplified throughout the description, figures, and examples. Any interpretation of the terms in this description should take into account the full description, figures, and examples presented herein.

The singular terms "a," "an," and "the" include the plural unless the context clearly dictates otherwise. Thus, for example, reference to an object can include multiple objects unless the context clearly dictates otherwise.

The terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

The term "about" refers to the range of values approximately near the given value in order to account for typical tolerance levels, measurement precision, or other variability of the embodiments described herein.

The term "specific capacity" refers to the amount (e.g., total or maximum amount) of electrons or lithium ions a material is able to hold (or discharge) per unit mass and can be expressed in units of mAh/g. In certain aspects and embodiments, specific capacity can be measured in a constant current discharge (or charge) analysis, which includes discharge (or charge) at a defined rate over a defined voltage range against a defined counter electrode. For example, specific capacity can be measured upon discharge at a rate of about 0.05 C (e.g., about 8.75 mA/g) from 4.45 V to 3.0 V versus a $Li/Li^+$ counter electrode. Other discharge rates and other voltage ranges also can be used, such as a rate of about 0.1 C (e.g., about 17.5 mA/g), or about 0.5 C (e.g., about 87.5 mA/g), or about 1.0 C (e.g., about 175 mA/g).

A rate "C" refers to either (depending on context) the discharge current as a fraction or multiple relative to a "1 C" current value under which a battery (in a substantially fully charged state) would substantially fully discharge in one hour, or the charge current as a fraction or multiple relative to a "1 C" current value under which the battery (in a substantially fully discharged state) would substantially fully charge in one hour.

The term "rated charge voltage" refers to an upper end of a voltage range during operation of a battery, such as a maximum voltage during charging, discharging, and/or cycling of the battery. In some aspects and some embodiments, a rated charge voltage refers to a maximum voltage upon charging a battery from a substantially fully discharged state through its (maximum) specific capacity at an initial cycle, such as the 1st cycle, the 2nd cycle, or the 3rd cycle. In some aspects and some embodiments, a rated charge voltage refers to a maximum voltage during operation of a battery to substantially maintain one or more of its performance characteristics, such as one or more of coulombic efficiency, retention of specific capacity, retention of energy density, and rate capability.

The term "rated cut-off voltage" refers to a lower end of a voltage range during operation of a battery, such as a minimum voltage during charging, discharging, and/or cycling of the battery. In some aspects and some embodiments, a rated cut-off voltage refers to a minimum voltage upon discharging a battery from a substantially fully charged state through its (maximum) specific capacity at an initial cycle, such as the 1st cycle, the 2nd cycle, or the 3rd cycle, and, in such aspects and embodiments, a rated cut-off voltage also can be referred to as a rated discharge voltage. In some aspects and some embodiments, a rated cut-off voltage refers to a minimum voltage during operation of a battery to substantially maintain one or more of its performance characteristics, such as one or more of coulombic efficiency, retention of specific capacity, retention of energy density, and rate capability.

The "maximum voltage" refers to the voltage at which both the anode and the cathode are fully charged. In an electrochemical cell, each electrode may have a given specific capacity and one of the electrodes will be the limiting electrode such that one electrode will be fully charged and the other will be as fully charged as it can be for that specific pairing of electrodes. The process of matching the specific capacities of the electrodes to achieve the desired capacity of the electrochemical cell is "capacity matching."

The term "NMC" refers generally to cathode materials containing $LiNi_xMn_yCo_zO_w$, where $x+y+z=1$ and $0<w<2$, and includes, but is not limited to, cathode materials containing $LiNi_{0.33}Mn_{0.33}Co_{0.33}O_2$, $LiNi_{0.5}Mn_{0.3}Co_{0.2}O_2$, (sometimes referred to as NMC (532)), and $LiNi_{0.6}Mn_{0.2}Co_{0.2}O_2$ (sometimes referred to as NMC (622)).

The term "LCO" refers generally to cathode materials containing $LiCo_pO_q$, such as $LiCoO_2$ or variations with elemental substitutions for the Li, Co, or O, where $0<p<4$ and $0<q<4$.

The term "matrix" (and the plural "matrices") refers to a relatively electrochemically inactive material. The matrix may be functionalized and added to the liquid electrolyte, which is functionalized such that the functional groups improve performance. The matrix may be a polymer or copolymer, a chemically crosslinked polymer or copolymer, a physically crosslinked polymer or copolymer due to hydrogen bonds, ionic interactions, or chain entanglements, or a rigid inorganic particulate structure.

The term "wt %" as used herein refers to the weight of the component as a percent of the total weight of the electrolyte formulation.

To the extent certain battery characteristics can vary with temperature, such characteristics are specified at room temperature (about 30 degrees C.), unless the context clearly dictates otherwise.

Ranges presented herein are inclusive of their endpoints. Thus, for example, the range 1 to 3 includes the values 1 and 3 as well as intermediate values.

FIG. 1 illustrates a lithium ion battery 100 implemented in accordance with an embodiment of the invention. The battery 100 includes an anode 102, a cathode 106, and a separator 108 that is disposed between the anode 102 and the cathode 106. In the illustrated embodiment, the battery 100 also includes a high voltage electrolyte 104, which is disposed within and between the anode 102 and the cathode 106 and remains stable during high voltage battery cycling.

The operation of the battery 100 is based upon reversible intercalation and de-intercalation of lithium ions into and from host materials of the anode 102 and the cathode 106. Other implementations of the battery 100 are contemplated, such as those based on conversion chemistry. Referring to FIG. 1, the voltage of the battery 100 is based on redox potentials of the anode 102 and the cathode 106, where lithium ions are accommodated or released at a lower potential in the former and a higher potential in the latter. To allow both a higher energy density and a higher voltage platform to deliver that energy, the cathode 106 includes an active cathode material for high voltage operations at or above 4.3V.

Examples of suitable high voltage cathode materials include phosphates, fluorophosphates, fluorosulfates, fluorosilicates, spinels, lithium-rich layered oxides, and composite layered oxides. Further examples of suitable cathode materials include: spinel structure lithium metal oxides, layered structure lithium metal oxides, lithium-rich layered structured lithium metal oxides, lithium metal silicates, lithium metal phosphates, metal fluorides, metal oxides, sulfur, and metal sulfides. Examples of suitable anode materials include conventional anode materials used in lithium ion batteries, such as lithium, graphite ("$Li_xC_6$"), and other carbon, silicate, or oxide-based anode materials.

According to certain embodiments of the invention, the electrolyte formulation can include one or more solvents and one or more salts, such as lithium-containing salts in the case of lithium ion batteries. Examples of suitable solvents include nonaqueous electrolyte solvents for use in lithium ion batteries, including carbonates, such as ethylene carbonate, dimethyl carbonate, ethyl methyl carbonate, propylene carbonate, methyl propyl carbonate, and diethyl carbonate; sulfones; silanes; nitriles; esters; ethers; and combinations thereof. The base electrolyte can also include small molecule additives.

The electrolyte formulations described herein can be used for a variety of batteries containing a high voltage cathode or a low voltage cathode, and in batteries operated at high temperatures. For example, the electrolyte formulations can be substituted in place of, or used in conjunction with, conventional electrolytes for lithium ion batteries for operations at or above 4.25 V. In particular, these additives are useful for lithium ion batteries containing NMC and/or LCO cathode materials.

Batteries including the electrolyte formulations can be conditioned by cycling prior to commercial sale or use in commerce. Such conditioning can include, for example, providing a battery, and cycling such battery through at least 1, at least 2, at least 3, at least 4, or at least 5 cycles, each cycle including charging the battery and discharging the battery at a given rate through a specified voltage range. Charging and discharging can be carried out at a higher or lower rate.

According to certain embodiments of the invention disclosed herein, functionalized matrix materials are added alone, in combination with other functionalized matrices, and/or in combination with other additives, to conventional electrolyte solutions containing solvents and salts. The addition of matrices to the electrolyte formulation improves the high temperature and/or high voltage performance during cycling of lithium ion electrochemical cells. Some functionalized matrices also showed unexpected synergistic effects when used in combinations with other additives.

According to certain embodiments of the invention, the matrix electrolyte additives used herein include a matrix material fabricated from a polymeric material or from an inorganic material. The polymer can be a polymer or copolymer and may be covalently, ionically, or physically cross-linked. In some preferred embodiments, the matrix additive is formed from a cross-linked organic polymer or silica and results in a suspension of insoluble material in the electrolyte solvents. In other embodiments, the additive is the fraction of the functionalized matrix that is soluble or sparingly soluble in the electrolyte.

Figure 2A:
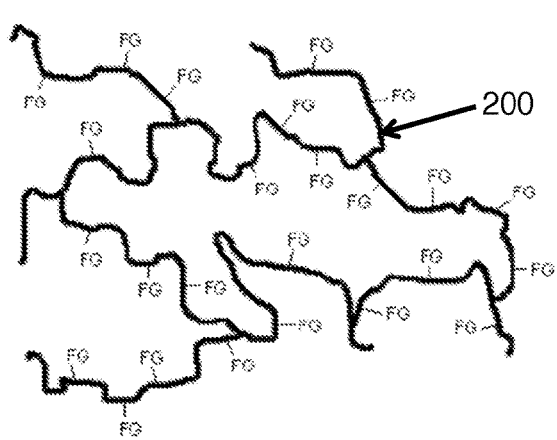
FIG. 2A illustrates a conceptual schematic of a microporous functionalized matrix.
Figure 2B:
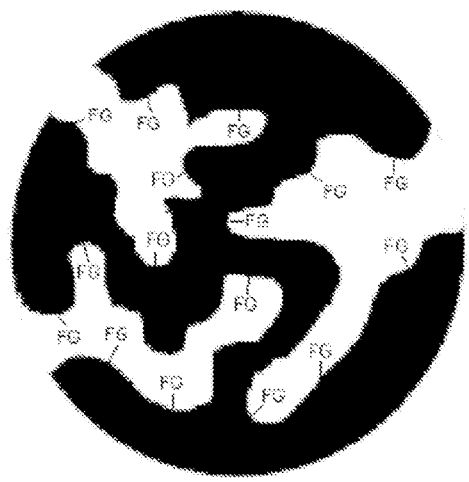
FIG. 2B illustrates a conceptual schematic of a macroporous functionalized matrix.

FIGS. 2A and 2B illustrate conceptual schematics of a microporous functionalized matrix (FIG. 2A) and a macroporous functionalized matrix (FIG. 2B). Polymer 200 forms a cross-linked matrix material and various functional groups FG may be embedded on and/or inside the matrix material. In some embodiments, the matrices are porous and have a high surface area. The functional groups in the matrix can have different capabilities or properties, such as to scavenge and/or immobilize undesirable components in the battery, such as the acids and transition metal ions described above. The inert polymer backbone provides chemical and electrochemical stability to the matrix material. Additionally, since many of the functional groups reside inside the pores of the matrix, the functional groups can resist decomposition. Due to the unique porous structure of the matrices, the dissolved transition metal ions, acids, trace amounts of water, or other undesirable compounds generated during battery cycling can be absorbed into those pores, largely reducing or even eliminating undesired side reactions.

Matrix materials for matrix additives as disclosed herein include, but are not limited to, polystyrene, styrene-divinyl benzene copolymer, poly-4-vinylpyridine, poly-4-vinylpyridine-divinyl benzene copolymer, polyaniline, cross-linked polyethylene oxide polymer and silicas.

Functional groups for matrices as disclosed herein include, but are not limited to, Bronsted or Lewis bases such as trialkyl ammonium hydroxides, pyridines, alkyl amines, arylamines, pyrimidines, diazaphosphorines. The functional groups could also be various heteroatom chelating ligands that could serve as transition metal scavengers, such as alkyl amines, mercaptalkyls, mercaptophenyl aminos, thios, imino diacetates, and imidazoles.

A distinguishing feature of preferred embodiments of the invention disclosed herein is that, unlike conventional electrolyte additives, the functionalized matrix additives in general have poor solubility in the electrolyte solvents. Common additives are soluble in electrolyte solvents at the concentrations typically used. In certain embodiments, a suspension of the functionalized matrix additives is used. That is, there is a sufficient concentration of the matrix added to the electrolyte formulation that the electrolyte formulation is cloudy and/or appears to have a particulate component. In other embodiments, a clear solution is obtained by filtration of a suspension. The clear solution still contains functionalized matrix additive, but at a concentration that renders the electrolyte formulation substantially clear to the unaided eye.

The amount of a particular functionalized matrix additive can be expressed in terms of a weight percent of the additive relative to a total weight of the electrolyte formulations (or wt %). For example, an amount of an additive can be in the range of about 0.01 wt % to about 30 wt %, such as from about 0.05 wt % to about 30 wt %, from about 0.01 wt % to about 20 wt %, from about 0.2 wt % to about 15 wt %, from about 0.2 wt % to about 10 wt %, from about 0.2 wt % to about 5 wt %, or from about 0.2 wt % to about 1 wt %, and, in the case of a combination of multiple additives, a total amount of the additives can be in the range of about 0.01 wt % to about 30 wt %, such as from about 0.05 wt % to about 30 wt %, from about 0.01 wt % to about 20 wt %, from about 0.2 wt % to about 15 wt %, from about 0.2 wt % to about 10 wt %, from about 0.2 wt % to about 5 wt %, or from about 0.2 wt % to about 1 wt %. An amount of an additive can refer to an initial amount of the additive used during the formation of the electrolyte formulations, or can refer to an initial amount of the additive within the electrolyte formulations prior to battery cycling (or prior to any significant amount of battery cycling), or can refer to the amount of additive used in the electrode fabrication.

In certain embodiments of the invention, the concentration of each additive in the electrolyte formulation is equal to about 5.0 wt %, 4.9 wt %, 4.8 wt %, 4.7 wt %, 4.6 wt %, 4.5 wt %, 4.4 wt %, 4.3 wt %, 4.2 wt %, 4.1 wt %, 4.0 wt %, 3.9 wt %, 3.8 wt %, 3.7 wt %, 3.6 wt %, 3.5 wt %, 3.4 wt %, 3.3 wt %, 3.2 wt %, 3.1 wt %, 3.0 wt %, 2.9 wt %, 2.8 wt %, 2.7 wt %, 2.6 wt %, 2.5 wt %, 2.4 wt %, 2.3 wt %, 2.2 wt %, or 2.1 wt %, 2.0 wt %, 1.9 wt %, 1.8 wt %, 1.7 wt %, 1.6 wt %, 1.5 wt %, 1.4 wt %, 1.3 wt %, 1.2 wt %, 1.1 wt %, 1.0 wt %, 0.9 wt %, 0.8 wt %, 0.7 wt %, 0.6 wt %, 0.5 wt %, 0.4 wt %, 0.3 wt %, 0.2 wt %, or 0.1 wt %. In certain embodiments of the invention, the concentration of functionalized matrix additive in the electrolyte formulation is in the range of about 5.0 wt % to about 0.1 wt %.

In certain embodiments of the invention, the concentration of each additive in the electrode formulation is equal to about 10.0 wt %, 9.9 wt %, 9.8 wt %, 9.7 wt %, 9.6 wt %, 9.5 wt %, 9.4 wt %, 9.3 wt %, 9.2 wt %, 9.1 wt %, 9.0 wt %, 8.9 wt %, 8.8 wt %, 8.7 wt %, 8.6 wt %, 8.5 wt %, 8.4 wt %, 8.3 wt %, 8.2 wt %, 8.1 wt %, 8.0 wt %, 7.9 wt %, 7.8 wt %, 7.7 wt %, 7.6 wt %, 7.5 wt %, 7.4 wt %, 7.3 wt %, 7.2 wt %, 7.1 wt %, 7.0 wt %, 6.9 wt %, 6.8 wt %, 6.7 wt %, 6.6 wt %, 6.5 wt %, 6.4 wt %, 6.3 wt %, 6.2 wt %, 6.1 wt %, 5.9 wt %, 5.8 wt %, 5.7 wt %, 5.6 wt %, 5.5 wt %, 5.4 wt %, 5.3 wt %, 5.2 wt %, 5.1 wt %, 5.0 wt %, 4.9 wt %, 4.8 wt %, 4.7 wt %, 4.6 wt %, 4.5 wt %, 4.4 wt %, 4.3 wt %, 4.2 wt %, 4.1 wt %, 4.0 wt %, 3.9 wt %, 3.8 wt %, 3.7 wt %, 3.6 wt %, 3.5 wt %, 3.4 wt %, 3.3 wt %, 3.2 wt %, 3.1 wt %, 3.0 wt %, 2.9 wt %, 2.8 wt %, 2.7 wt %, 2.6 wt %, 2.5 wt %, 2.4 wt %, 2.3 wt %, 2.2 wt %, or 2.1 wt %, 2.0 wt %, 1.9 wt %, 1.8 wt %, 1.7 wt %, 1.6 wt %, 1.5 wt %, 1.4 wt %, 1.3 wt %, 1.2 wt %, 1.1 wt %, 1.0 wt %, 0.9 wt %, 0.8 wt %, 0.7 wt %, 0.6 wt %, 0.5 wt %, 0.4 wt %, 0.3 wt %, 0.2 wt %, or 0.1 wt %. In certain embodiments of the invention, the concentration of functionalized matrix additive in the electrode formulation is in the range of about 10.0 wt % to about 0.1 wt % of the active materials.

Resulting performance characteristics of a battery can depend upon the identity of a particular additive used to form the high voltage electrolyte, an amount of the additive used, and, in the case of a combination of multiple additives, a relative amount of each additive within the combination. Accordingly, the resulting performance characteristics can be fine-tuned or optimized by proper selection of the additives and adjusting amounts of the additives.

The electrolyte formulations can be prepared using a variety of techniques, such as by mixing a conventional electrolyte and the functionalized matrix additives, dispersing the additives within a conventional electrolyte resulting in a suspension, or dispersing the additives with a conventional electrolyte for a certain amount of time followed by a filtration resulting in a clear solution, or otherwise placing these components in contact with one another. The additives can be provided in a liquid form, a powdered form (or another solid form), or a combination thereof. The additives can be incorporated in the electrolyte formulations prior to, during, or subsequent to battery assembly.

The matrix additives disclosed herein can effectively improve the high temperature cycle life of lithium ion battery cells, especially when cells are cycled at high voltages (such as greater than 4.25 V) without negative impact on initial reversible capacity and columbic efficiency. Without being bound to any particular hypothesis or mechanism of action, the matrix additives may improve the high temperature cycle life by scavenging and/or immobilizing detrimental species such as $H^+$, Lewis acids, and/or leached transition metal ions originally present in the electrolyte and/or generated during cycling. These undesirable compounds can trigger parasitic reactions, including parasitic reactions occurring on the SEI on electrode surfaces.

Other mechanisms of action of the electrolyte are contemplated. For example, one or more additives or a derivative thereof (e.g., their decomposition product) can form or improve the quality of the cathode or anode SEI, such as to reduce the resistance for lithium ion diffusion through the anode SEI. As another example, one or more additives or a derivative thereof (e.g., their decomposition product) can improve the stability of the electrolyte by chemically reacting or forming a complex with other electrolyte components.

In some embodiments, the relative insolubility, or poor solubility, of the matrix additive can be used advantageously in a cathode formulation. Adding matrix additives to the electrode formulation process can result in cast electrode films that have the favorable properties of the matrix materials described herein but are not present in the electrolyte formulation. In some embodiments, both the electrode and the electrolyte can include matrix additives.

In some embodiments, the matrix additives can be added into a slurry with a liquid component, along with the other components for cathode formation such as active material (for example, NMC or LCO), binder, and conductive filler. The matrices can be added to the electrode formation process by premixing the powdered materials or by adding the matrix (in dry or suspension form) to the slurry of cathode components.

In some embodiments, the matrix additives can be added into a slurry with a liquid component, along with the other components for anode formation such as active material (for example, graphite, lithium titanate, silicon), binder, and conductive filler. The matrix additives can be added to the electrode formation process by premixing the powdered materials or by adding the matrix (in dry or suspension form) to the slurry of anode components.

One of the advantages of formulating the matrix additive into the cathode or anode film is that the matrix additive can still contact the electrolyte and function as if it was an electrolyte additive during cycling. The matrix additive will also be in direct contact with the cathode materials, which may help to reduce transition metal dissolution and to consume dissolved transition metal ions before they transport to the anode. In some embodiments, the matrix additive can be included during the anode formation process and achieve similar benefits.

In some embodiments, the matrix additives can be added into a liquid solution. The separator/electrode films could be soaked with these solutions, followed by heat treatment or UV irradiation. The heat or UV initiated polymerization could help to form thin, cross-linked polymer layers on separator/electrode surface.

The following examples describe specific aspects of some embodiments of the invention to illustrate and provide a description for those of ordinary skill in the art. The examples should not be construed as limiting the invention, as the examples merely provide specific methodology useful in understanding and practicing some embodiments of the invention.

EXAMPLES

Electrochemical Cell Construction. Battery cells were formed in a high purity Argon filled glove box (M-Braun, $O_2$ and humidity content <0.1 ppm). The electrodes were prepared by the following methods. (i) For the cathode, a commercial cathode material was mixed with poly(vinylidene fluoride) (Sigma Aldrich) and carbon black (Super P Li, TIMCAL) with 1-methyl-2-pyrrolidinone (Sigma Aldrich) as solvent. The resulting slurry was deposited on an aluminum current collector and dried to form a composite cathode film. (ii) For the anode, a graphitic carbon was mixed with poly(vinylidene fluoride) (Sigma Aldrich) and carbon black (Super P Li, TIMCAL) with 1-methyl-2-pyrrolidinone (Sigma Aldrich) as solvent. The resulting slurry was deposited on a copper current collector and dried to form a composite anode film. Each battery cell included the composite cathode film, a polypropylene separator, and the composite anode film. Electrolyte formulations were prepared by adding 2 weight % of matrix additive to EC/EMC (1:2 by volume) with 1M $LiPF_6$. The mixture was stored inside an argon glovebox for at least 24 hours before use. The electrolyte formulations were added to the battery cell. The battery cell was sealed and cycled using the following protocols. Electrolyte formulations in the form of both suspensions and clear solutions (obtained from filtering the suspensions) were tested. All results are averages of at least two cells.

SEI Formation and High Temperature Cycling. The formation cycle for cells having an NCM (523) cathode is done at 30 degrees Celsius and includes a 12 hour open circuit voltage (OCV) hold followed by a C/20 charge to 4.35 V or 4.4V with a constant voltage (CV) hold until the charge current is less than 0.02 C. The cell is then discharged at C/20 discharge to 3.0V. This multistep process was repeated twice to complete the formation cycle. Cells were then heated up to 50 degrees Celsius and cycled between 4.35V and 3V or between 4.4V and 3V at a 1 C cycling rate.

The formation cycle for cells having an NCM (622) cathode is done at 30 degrees Celsius and includes a 12 hour open circuit voltage (OCV) hold followed by a C/20 charge to 4.4 V with a constant voltage (CV) hold until the charge current is less than 0.02 C. The cell is then discharged at C/20 discharge to 3.0V. This multistep process was repeated twice to complete the formation cycle. Cells were then heated up to 50 degrees Celsius and cycled between 4.4 V and 3V at a 1 C cycling rate.

The formation cycle for certain cells having an LCO cathode is done at 30 degrees Celsius and includes a 12 hour open circuit voltage (OCV) hold followed by a C/20 charge to 4.25 V with a constant voltage (CV) hold until the charge current is less than 0.02 C. The cell is then discharged at C/20 discharge to 3.0V. This multistep process was repeated twice to complete the formation cycle. Cells were then heated up to 50 degrees Celsius and cycled between 4.25 V and 3V at a 1 C cycling rate.

The formation cycle for certain LCO cells was 12 hours OCV hold, followed by a C/20 charge to 4.45 V with a CV hold until the charge current is smaller than 0.02 C, and then a C/20 discharge to 3.0V at 30 degrees Celsius. The process was repeated twice to complete the formation cycle. Cells were then heated up to 45 degrees Celsius and cycled between 4.45 V and 3V with 0.5 C charging rate and 1 C discharging rate.

Cathode Additives. A specified amount of matrix additive, such as 5 weight % of the total cathode formulation weight, was added to the cathode mixture described above. As a specific example, the ratio of NCM (622) active material (including the matrix additive) to binder and carbon can be 90:5:5. The fabricated electrodes were tested in the same protocols as described above.

TABLE 1

Chemical information for certain matrix additives

| Matrix ID | Product Name | Matrix | Functional Group |
|---|---|---|---|
| 2 | Ambersep 900 OH OH(−)-Form | styrene divinyl benzene copolymer | benzyl, trimethyl ammonium hydroxide |
| 4 | Reillex 402 ion-exchange resin, 2% cross-linked with divinylbenzene | poly-4-vinylpyridine divinyl benzene copolymer (2% crosslinked) | pyridine |
| 7 | Aminomethyl Chemmatrix resin | cross-linked polyethylene oxide polymer | primary alkyl amines |
| 2232 | Polyaniline | Polyaniline | arylamine |
| 2233 | 1,3,4,6,7,8-Hexahydro-2H-pyrimido[1,2-a]pyrimidine, polymer-bound | styrene divinyl benzene copolymer | pyrimidine |
| 2235 | Piperidinomethyl) poly styrene | styrene divinyl benzene copolymer | piperidine |
| 2236 | QuadraPure ® Aminomethyl phosphonic acid | styrene divinyl benzene copolymer | Aminomethyl phosphonic |
| 2241 | QuadraSil ® Mercaptopropyl | Silica | mercaptopropyl |
| 2242 | QuadraSil ® Aminopropyl | Silica | amino propyl |

Figures 3A, 3B:
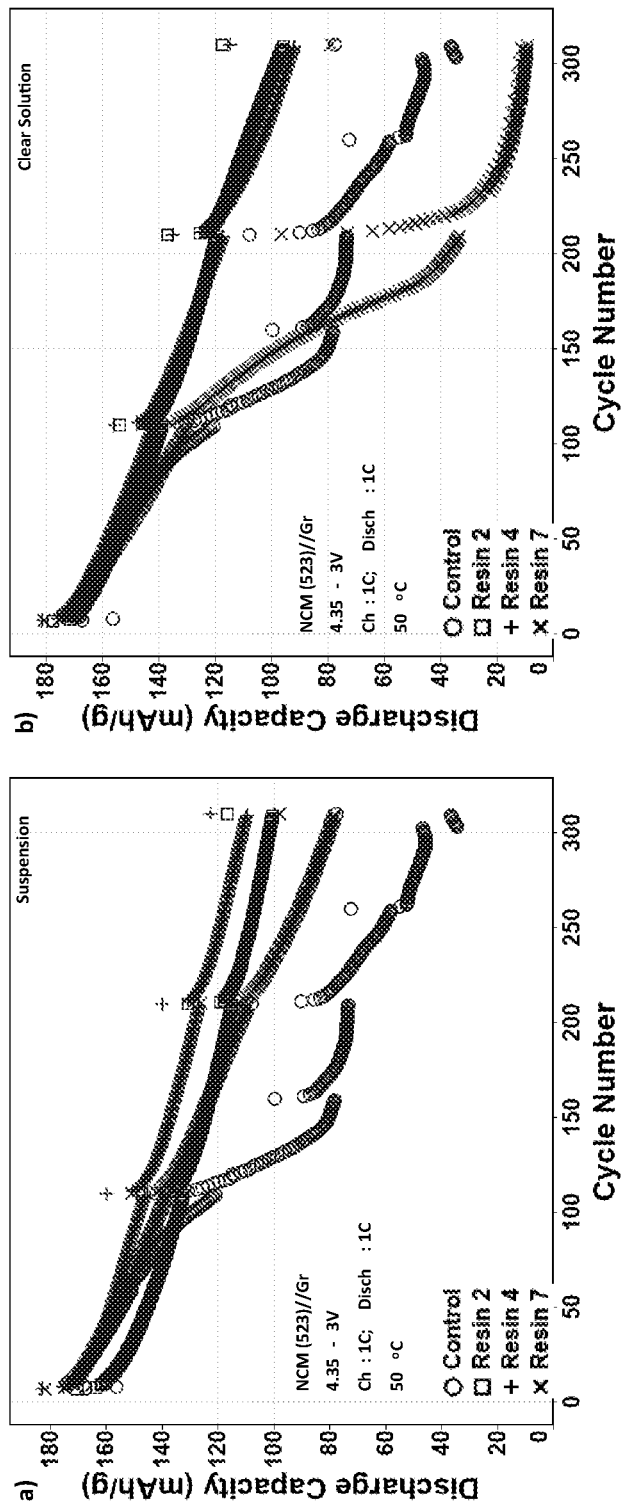
FIG. 3A illustrates electrochemical characterization of the discharge capacity versus cycle number for various electrolytes formulations in electrochemical cells having an NMC (523) cathode and a graphite anode.
FIG. 3B illustrates electrochemical characterization of the discharge capacity versus cycle number for various electrolytes formulations in electrochemical cells having an NMC (523) cathode and a graphite anode.

FIGS. 3A and 3B illustrate electrochemical characterization of the discharge capacity versus cycle number for various electrolytes formulations in electrochemical cells having an NMC (523) cathode and a graphite anode. FIG. 3A illustrates the characterization of cells where the electrolyte formulation was in the form of a suspension of matrix additives in the electrolyte solvent. FIG. 3B illustrates the characterization of cells where the electrolyte formulation was in the form of a clear solution of matrix additives in the electrolyte solvent.

FIG. 3A shows that the electrolyte formulations with matrix suspensions showed up to 63% capacity retention after 300 cycles at 50 degrees Celsius while the control cells with baseline electrolyte (no additives) showed only 23% capacity retention. All of the electrolyte formulations with matrix suspensions performed better than the control. FIG. 3B shows that two of the three electrolyte formulations with matrix additives in a clear solution showed capacity retention improvement after 300 cycles at 50 degrees Celsius as compared with baseline electrolyte.

Figure 4A:
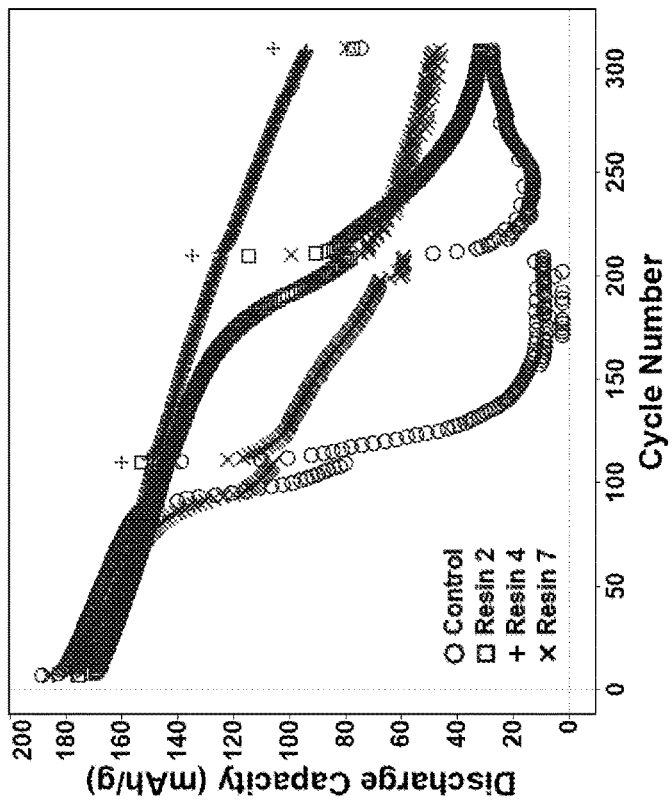
FIG. 4A illustrates electrochemical characterization of the discharge capacity versus cycle number for various electrolytes formulations in electrochemical cells having an NMC (622) cathode and a graphite anode.
Figure 4B:
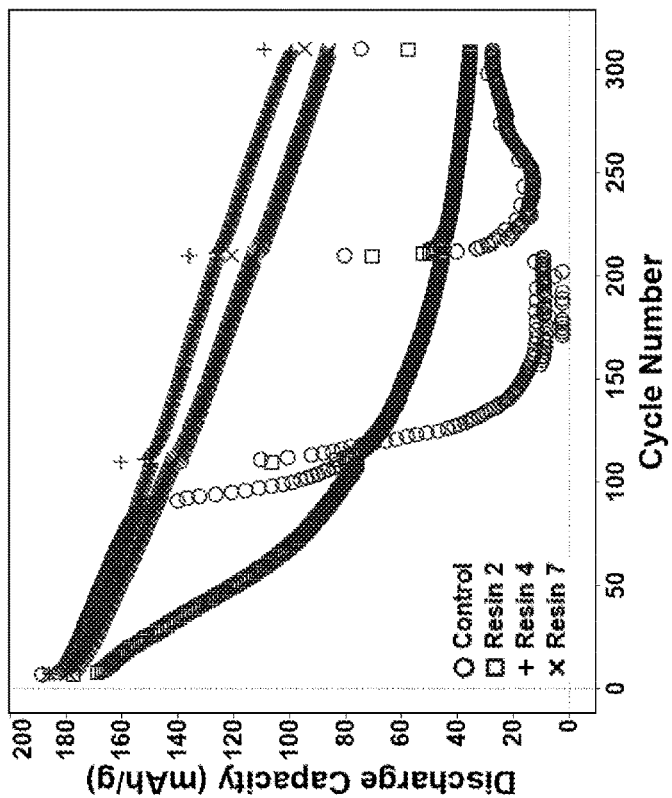
FIG. 4B illustrates electrochemical characterization of the discharge capacity versus cycle number for various electrolytes formulations in electrochemical cells having an NMC (622) cathode and a graphite anode.

FIGS. 4A and 4B illustrate electrochemical characterization of the discharge capacity versus cycle number for various electrolytes formulations in electrochemical cells having an NMC (622) cathode and a graphite anode. FIG. 4A illustrates the characterization of cells where the electrolyte formulation was in the form of a suspension of matrix additives in the electrolyte solvent. FIG. 4B illustrates the characterization of cells where the electrolyte formulation was in the form of a clear solution of matrix additives in the electrolyte solvent.

FIG. 4A shows that the electrolyte formulations with matrix suspensions showed up to 53% capacity retention after 300 cycles at 50 degrees Celsius while the control cells with baseline electrolyte (no additives) showed only 15% capacity retention. All of the electrolyte formulations with matrix suspensions performed better than the control. FIG. 4B shows that the three electrolyte formulations with matrix additives in a clear solution showed capacity retention improvement after 300 cycles at 50 degrees Celsius as compared with baseline electrolyte.

Figure 5A:
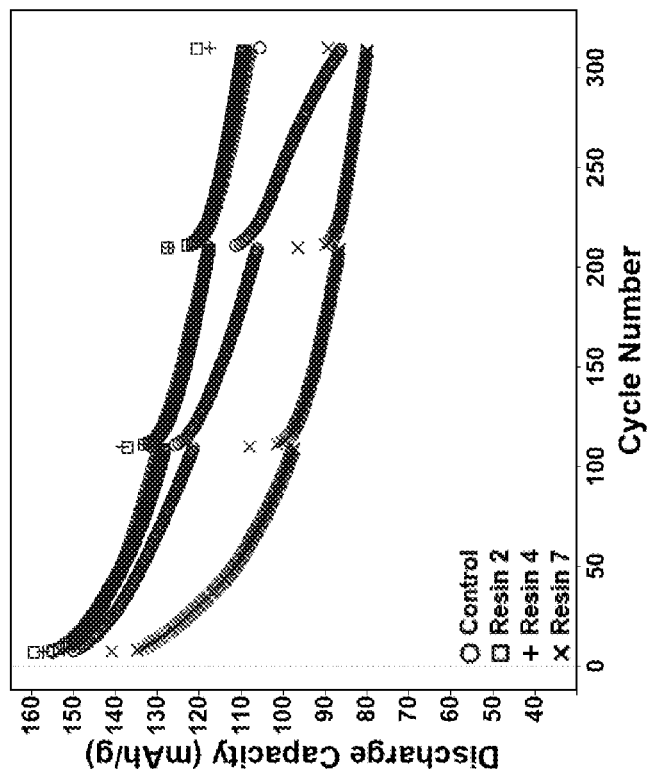
FIG. 5A illustrates electrochemical characterization of the discharge capacity versus cycle number for various electrolytes formulations in electrochemical cells having an LCO cathode and a graphite anode.
Figure 5B:
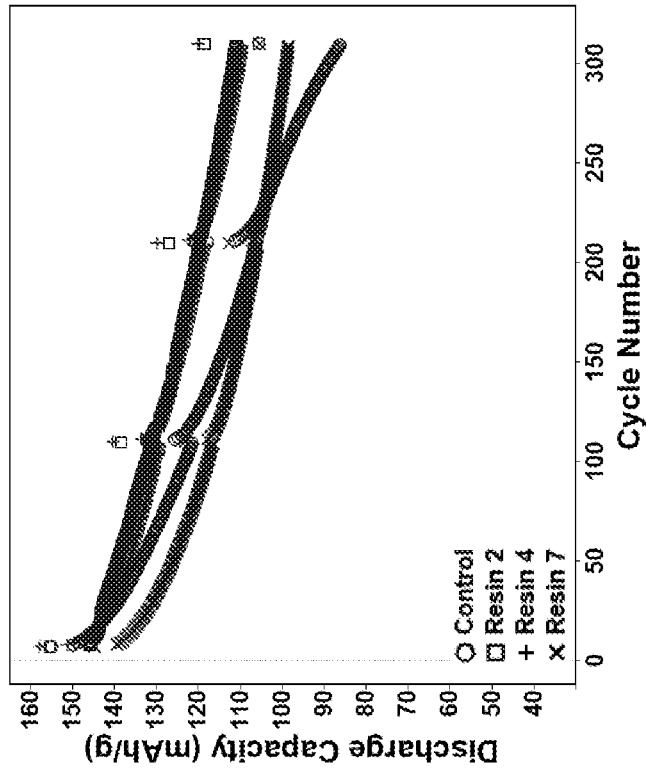
FIG. 5B illustrates electrochemical characterization of the discharge capacity versus cycle number for various electrolytes formulations in electrochemical cells having an LCO cathode and a graphite anode.

FIGS. 5A and 5B illustrate electrochemical characterization of the discharge capacity versus cycle number for various electrolytes formulations in electrochemical cells having an LCO cathode and a graphite anode. FIG. 5A illustrates the characterization of cells where the electrolyte formulation was in the form of a suspension of matrix additives in the electrolyte solvent. FIG. 5B illustrates the characterization of cells where the electrolyte formulation was in the form of a clear solution of matrix additives in the electrolyte solvent.

FIG. 5A shows that the electrolyte formulations with matrix suspensions showed up to 76% capacity retention after 300 cycles at 50 degrees Celsius while the control cells with baseline electrolyte (no additives) showed only 56% capacity retention. Some of the electrolyte formulations with matrix suspensions performed better than the control. FIG. 5B shows that some of the electrolyte formulations with matrix additives in a clear solution showed capacity retention improvement after 300 cycles at 50 degrees Celsius as compared with baseline electrolyte.

Figures 6A, 6B:
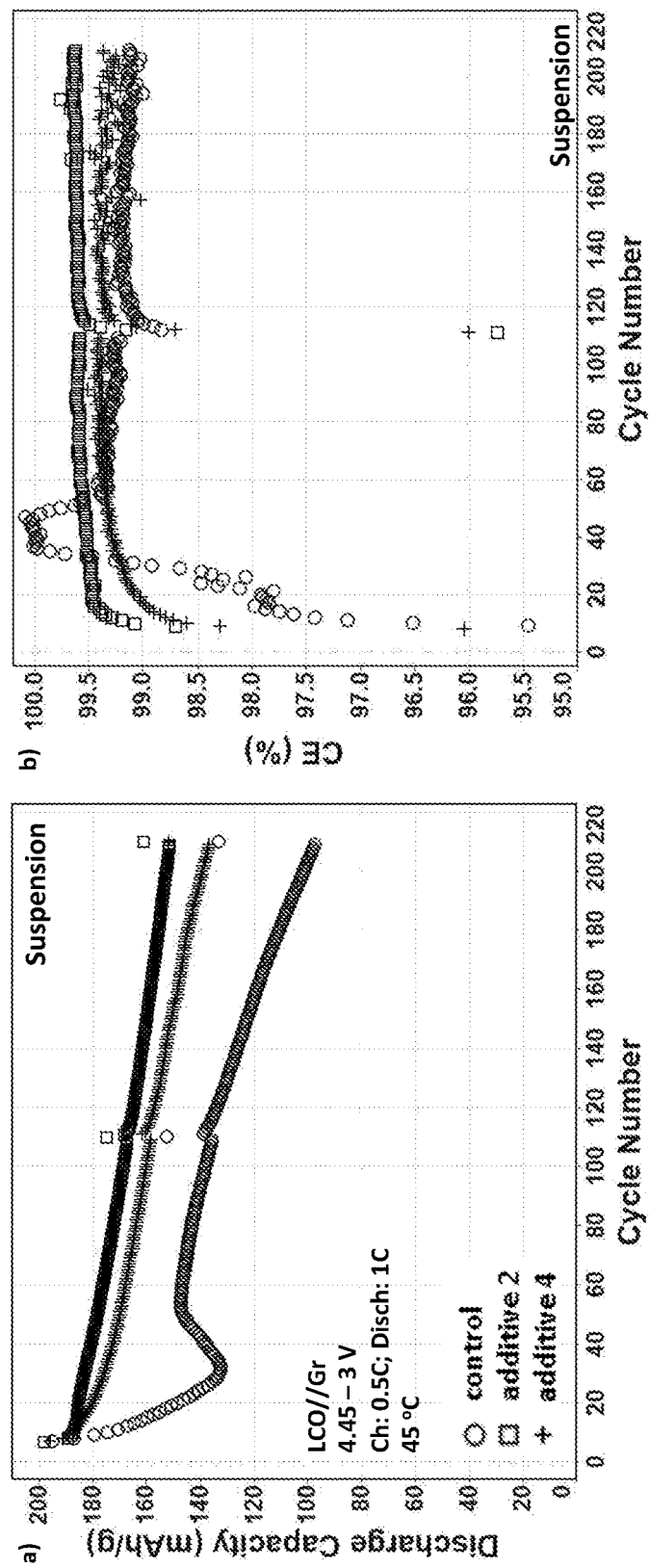
FIG. 6A illustrates electrochemical characterization of the discharge capacity versus cycle number for various electrolytes formulations in electrochemical cells having a high voltage LCO cathode and a graphite anode.
FIG. 6B illustrates electrochemical characterization of the coulombic efficiency versus cycle number for various electrolytes formulations in electrochemical cells having a high voltage LCO cathode and a graphite anode.

FIGS. 6A and 6B illustrate electrochemical characterization of the discharge capacity versus cycle number and columbic efficiency versus cycle number for various electrolytes formulations in electrochemical cells having an LCO cathode and a graphite anode. FIG. 6A illustrates the characterization of cell the discharge capacity versus cycle number where the electrolyte formulation was in the form of a suspension of matrix additives in the electrolyte solvent. FIG. 6B illustrates the characterization of cell columbic efficiency versus cycle number for the same sets of cells.

FIG. 6A shows that the electrolyte formulations with matrix suspensions showed up to 80% capacity retention after 200 cycles at 45 degrees Celsius while the control cells with baseline electrolyte (no additives) showed only 52% capacity retention. FIG. 6B shows that the electrolyte formulations with matrix suspensions showed much improved columbic efficiency than the baseline electrolyte almost all the time during the first 200 cycles.

Figure 7B:
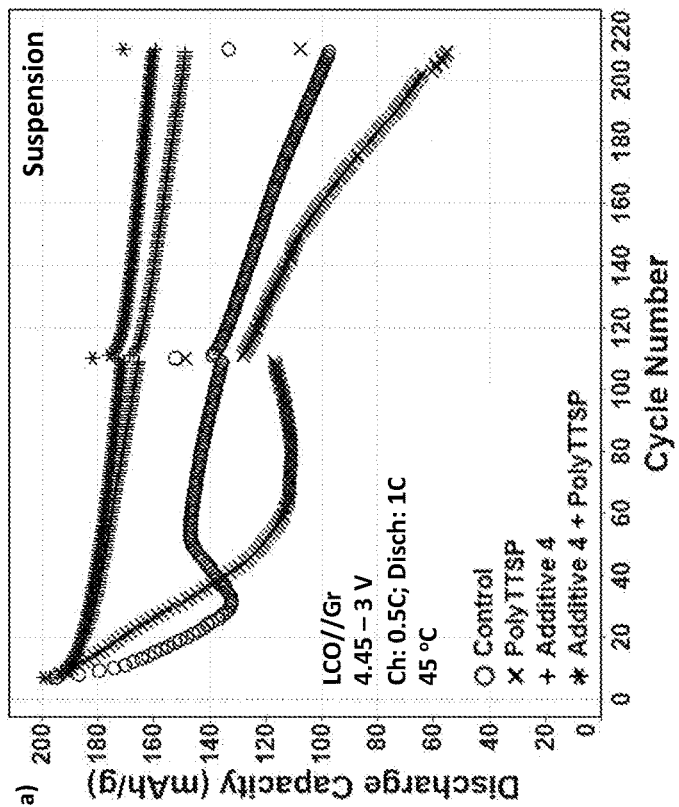
FIG. 7B illustrates electrochemical characterization of the discharge capacity versus cycle number for various electrolytes formulations in electrochemical cells having an LCO cathode and a graphite anode or NMC (523) cathode and a graphite anode.
Figure 7A:
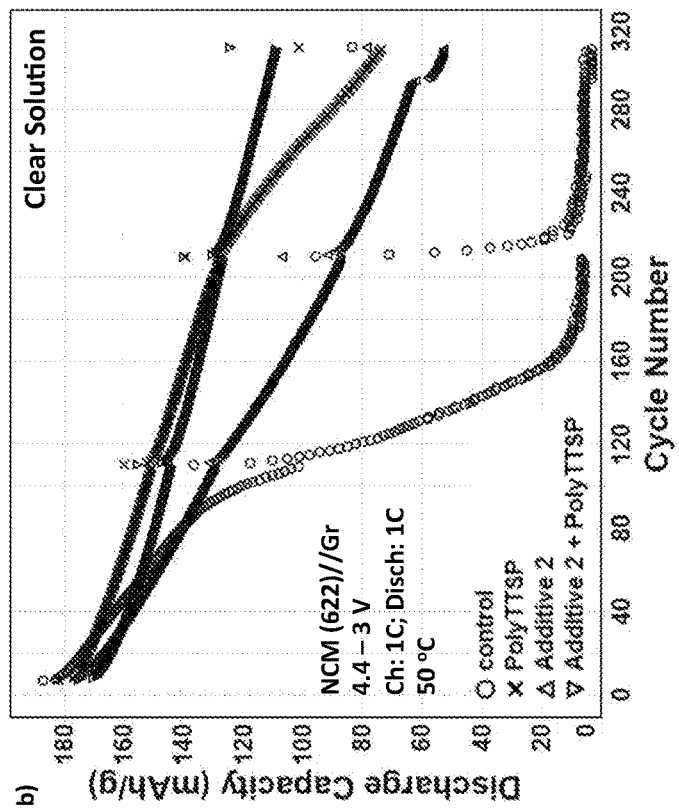
FIG. 7A illustrates electrochemical characterization of the discharge capacity versus cycle number for various electrolytes formulations in electrochemical cells having an LCO cathode and a graphite anode or NMC (523) cathode and a graphite anode.

FIG. 7A shows that the electrolyte formulations with Matrix 4 suspensions and poly(trimethylsilylphosphate) (PolyTMSP) showed synergistic effects for high voltage cycling performance in LCO and graphite full cells. The cells with both additives showed better performance than cells with either single additive. The cells showed 83%, 77%, and 29% capacity retention after 200 cycles at 45 degrees Celsius for cells with both additives, with only Matrix 4, and with only PolyTMSP, respectively. FIG. 7B shows that the electrolyte formulations with Matrix 2 suspensions and PolyTMSP showed synergistic effects on high voltage cycling performance in NMC and graphite full cells. The cells with both additives showed better performance than cells with either single additive. The cells showed 64%, 30%, and 42% capacity retention after 300 cycles at 50 degrees Celsius for cells with both additives, with only Matrix 2, and with only PolyTMSP, respectively.

Figure 8:
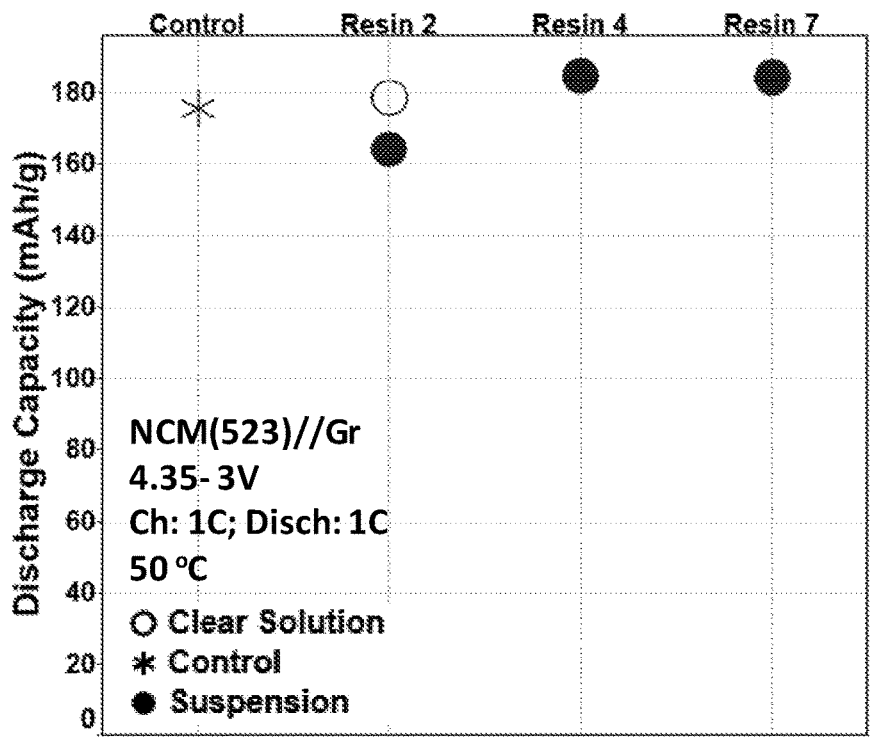
FIG. 8 illustrates the initial electrochemical characterization of an electrochemical cell assembled to contain an electrolyte formulation having certain additives as disclosed herein.
Figure 9:
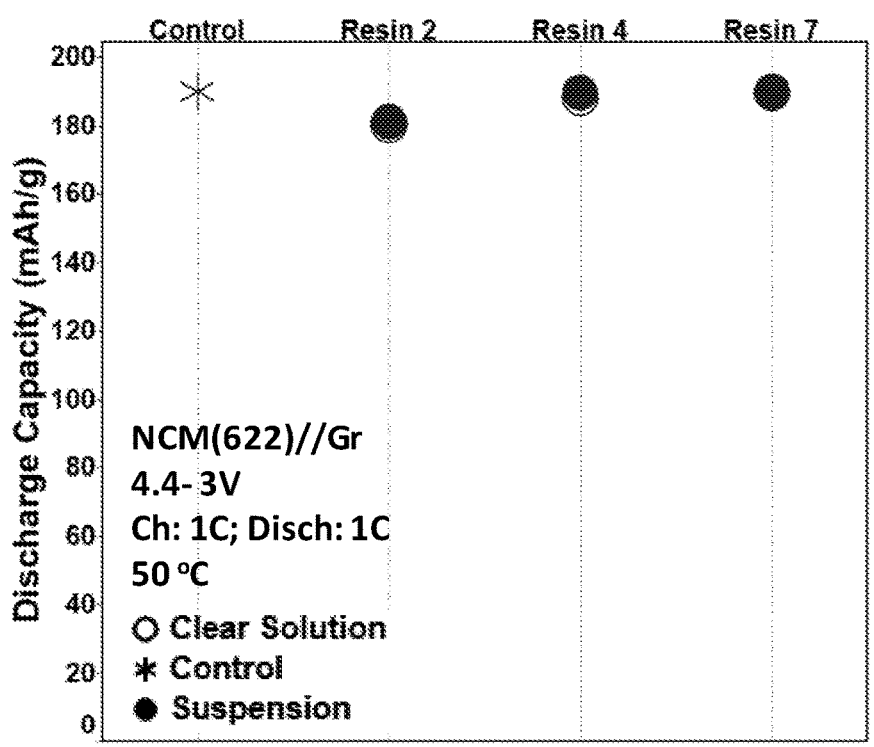
FIG. 9 illustrates the initial electrochemical characterization of an electrochemical cell assembled to contain an electrolyte formulation having certain additives as disclosed herein.
Figure 10:
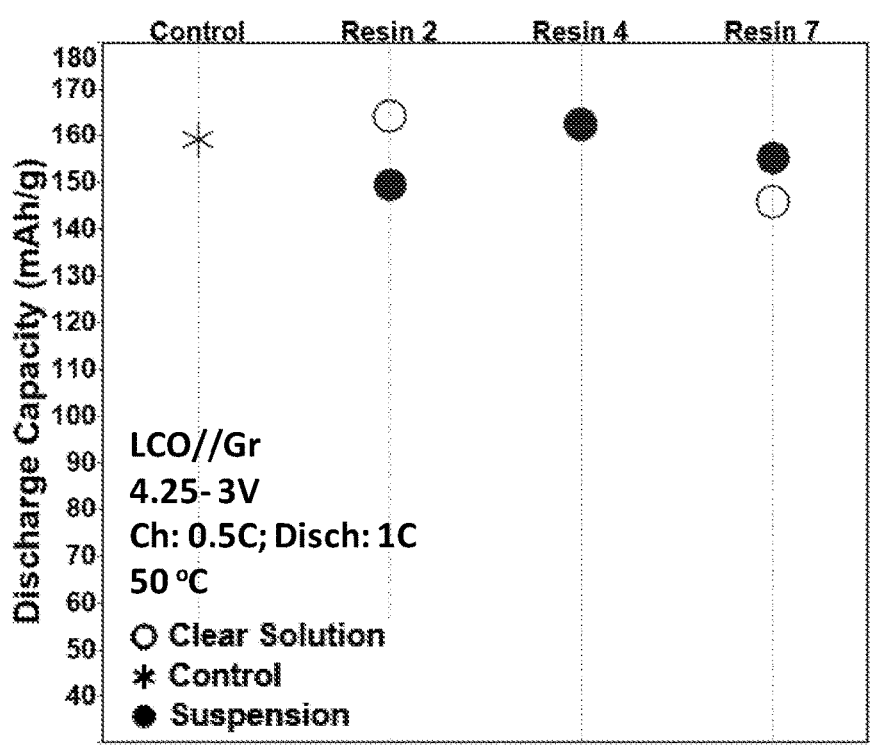
FIG. 10 illustrates the initial electrochemical characterization of an electrochemical cell assembled to contain an electrolyte formulation having certain additives as disclosed herein.

FIGS. 8, 9, and 10 illustrate testing of initial discharge capacity for cells having electrolyte formulations with matrix additives. FIG. 8 illustrates the testing of an electrochemical cell having an NMC (523) cathode, FIG. 9 illustrates the testing of an electrochemical cell having an NMC (622) cathode, and FIG. 10 illustrates the testing of an electrochemical cell having an LCO cathode. In each case, the data show that there is not negative effect on initial discharge capacity using the electrolyte formulations with matrix additives as compared to the control electrolytes.

Thus, the matrix additives disclosed herein can improve the capacity retention over 300 cycles without sacrificing initial discharge capacity.

Table 2 summarizes the electrochemical cycling performance of various additives with different matrices and functional groups (see Table 1 for the matrix and functional group identities referenced in Table 2).

TABLE 2

Electrochemical performance summary for certain matrix additives

| Matrix ID | Cycle 1 Capacity (mAh/g) | Cycle 1 Coulombic Efficiency (%) | Initial High Temperature Capacity (mAh/g) | Capacity retention (%, Cycle 300) |
|---|---|---|---|---|
| none | 192.6 | 87.1 | 182.1 | 5.4 |
| 2233 | 188.8 | 86.9 | 172.5 | 51 |
| 2235 | 191.6 | 87.2 | 182.5 | 52 |
| 2236 | 181.9 | 83.4 | 171.8 | 58 |
| 2241 | 178.5 | 81.8 | 164.7 | 62 |
| 2242 | 191.3 | 86.7 | 179.7 | 46 |

As shown in Table 2, all the matrix additives showed significant high voltage high temperature cycle life improvement for full cells formed from an NMC (523) cathode and graphite anode. The cells were cycled between 4.4 V to 3 V at 50 degrees Celsius. Cells were charged and discharged with 1 C cycling rate.

Figures 11A, 11B:
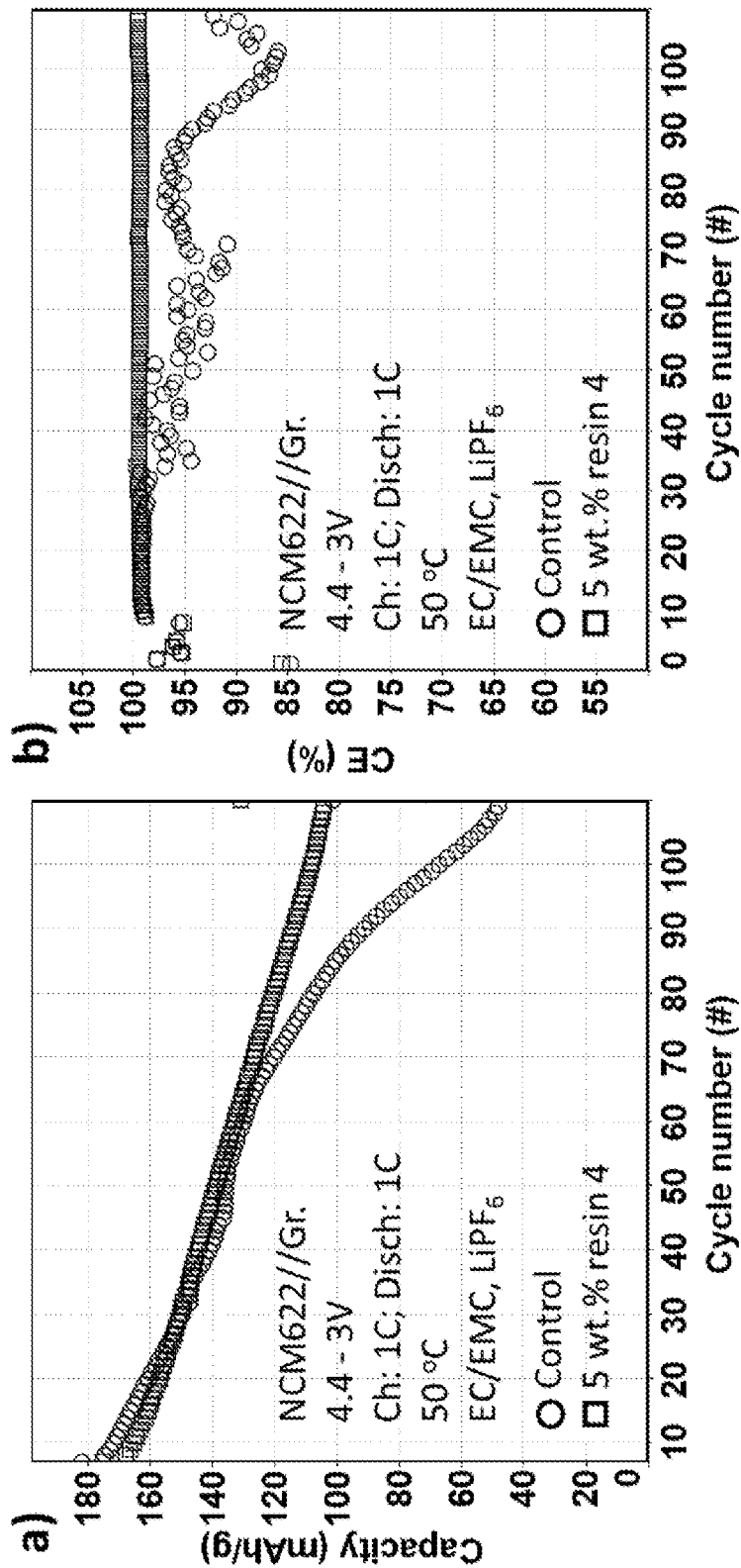
FIG. 11A illustrates electrochemical characterization of the coulombic efficiency versus cycle number for various electrode formulations in electrochemical cells having an NMC (622) cathode and a graphite anode.
FIG. 11B illustrates electrochemical characterization of the coulombic efficiency versus cycle number for various electrode formulations in electrochemical cells having an NMC (622) cathode and a graphite anode.

FIGS. 11A and 11B illustrate electrochemical characterization of the discharge capacity versus cycle number and coulombic efficiency versus cycle number for various electrode formulations in electrochemical cells having an NMC (622) cathode and a graphite anode. FIG. 11A illustrates a significant improvement in capacity retention for the cathode formulated with a matrix additive. In this case, the cathode including Matrix 4 showed no change in the capacity while the control demonstrated a dramatic capacity fade after about 70 cycles. FIG. 11B illustrates that the cathode formulated with a matrix additive demonstrated improved coulombic efficiency as compared to the control cathode. The coulombic efficiency of the cathode formulated with a matrix additive was stable at about 99.5% for the duration of the test while the coulombic efficiency of the control material degraded, including large fluctuations, after cycle 30.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, or process to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A battery comprising:
   an anode comprising an anode active material;
   a cathode comprising a cathode active material;
   a liquid electrolyte comprising a lithium salt, a non-aqueous solvent; and
   a polymer matrix additive comprising an inert polymer backbone and insoluble in the non-aqueous solvent, wherein the polymer matrix additive is present within at least one of the anode or the cathode such that one or more of the polymer matrix additives are each independently selected from any other polymer matrix additive.

2. The battery of claim 1 wherein one or more of the polymer matrix additives comprises a functionalized polymer.

3. The battery of claim 1 wherein one or more of the polymer matrix additives comprises a functionalized copolymer.

4. The battery of claim 1 wherein one or more of the polymer matrix additives comprises a vinyl polymer.

5. The battery of claim 1 wherein one or more of the polymer matrix additives comprises a styrene polymer.

6. The battery of claim 1 wherein one or more of the polymer matrix additives comprises a styrene divinyl benzene copolymer.

7. The battery of claim 1 wherein one or more of the polymer matrix additives comprises a poly-4-vinylpyridine divinyl benzene copolymer.

8. The battery of claim 1 one or more of the polymer matrix additives comprises an alkene polymer.

9. The battery of claim 1 wherein the polymer matrix additive comprises a polyethylene oxide polymer.

10. The battery of claim 1 comprising an additional matrix additive comprising silica.

11. The battery of claim 1 wherein one or more of the polymer matrix additives comprises a benzyl group.

12. The battery of claim 1 wherein one or more of the polymer matrix additives comprises a trimethyl ammonium hydroxide group.

13. The battery of claim 1 wherein one or more of the polymer matrix additives comprises a pyridine group.

14. The battery of claim 1 wherein one or more of the polymer matrix additives comprises an alkyl amine group.

15. The battery of claim 1 wherein the cathode comprises cobalt.

16. The battery of claim 1 wherein the cathode comprises nickel, manganese, and cobalt.

17. The battery of claim 1 wherein electrolyte further comprises poly(trimethylsilylphosphate).

18. The battery of claim 1 further comprising a separator, wherein the polymer matrix additive is adhered to the separator.

19. The battery of claim 1 wherein the polymer matrix additive is present only in the anode or the cathode.

* * * * *